US011123329B1

(12) United States Patent
Dalsgaard et al.

(10) Patent No.: US 11,123,329 B1
(45) Date of Patent: Sep. 21, 2021

(54) USE OF ANGIOTENSIN II TYPE 2 RECEPTOR AGONIST

(71) Applicant: Vicore Pharma AB, Stockholm (SE)

(72) Inventors: Carl-Johan Dalsgaard, Stockholm (SE); Johan Raud, Stockholm (SE); Rohit Batta, Stockholm (SE)

(73) Assignee: VICORE PHARMA AB, Stockholm (SE)

( * ) Notice: Subject to any disclaimer, the term of this patent is extended or adjusted under 35 U.S.C. 154(b) by 0 days.

(21) Appl. No.: 17/113,416

(22) Filed: Dec. 7, 2020

(30) Foreign Application Priority Data

Mar. 23, 2020 (GB) ..................................... 2004209
Jun. 23, 2020 (GB) ..................................... 2009574

(51) Int. Cl.

| | | |
|---|---|---|
| *A61K 31/4178* | (2006.01) | |
| *A61P 31/14* | (2006.01) | |
| *A61K 31/16* | (2006.01) | |
| *A61K 31/573* | (2006.01) | |
| *A61K 38/21* | (2006.01) | |
| *A61K 45/06* | (2006.01) | |
| *A61K 31/513* | (2006.01) | |
| *A61K 31/7056* | (2006.01) | |
| *A61K 31/706* | (2006.01) | |

(52) U.S. Cl.
CPC .......... *A61K 31/4178* (2013.01); *A61K 31/16* (2013.01); *A61K 31/513* (2013.01); *A61K 31/573* (2013.01); *A61K 31/706* (2013.01); *A61K 31/7056* (2013.01); *A61K 38/215* (2013.01); *A61K 45/06* (2013.01); *A61P 31/14* (2018.01)

(58) Field of Classification Search
None
See application file for complete search history.

(56) References Cited

U.S. PATENT DOCUMENTS

| 2008/0159962 | A1 | 7/2008 | Penninger et al. |
| 2018/0078529 | A1 | 3/2018 | Dahlöf et al. |

FOREIGN PATENT DOCUMENTS

| EP | 1723962 A1 | 11/2006 |
| WO | 2002/096883 A1 | 12/2002 |
| WO | 2016/139475 A1 | 9/2016 |
| WO | 2020/095042 A1 | 5/2020 |

OTHER PUBLICATIONS

Weston et al., "Respiratory Viruses", Elsevier, Encyclopedia of Microbiology, 4th Edition, 2019, pp. 85-101 (Year: 2019).*

Soheili et al., "Combination of C21 and ARBs with rhACE2 as a Therapeutic Protocol: A New Promising Approach for Treating ARDS in Patients with Coronavirus Infection," Med J Islam Repub Iran 34:120 (2020).
Liu et al., "Clinical and Biochemical Indexes from 2019-nCoV Infected Patients Linked to Viral Loads and Lung Injury," Science China Life Sciences 63(3)364-374 (2020).
Chamoux et al., "Involvement of the Angiotensin II Type 2 Receptor in Apoptosis During Human Fetal Adrenal Gland Development," J Clin Endocrinol Metab 84(12):4722-4730 (1999).
Diaz, "Hypothesis: Angiotensin-Converting Enzyme Inhibitors and Angiotensin Receptor Blockers May Increase the Risk of Severe COVID-19," Journal of Travel Medicine 1-2 (2020).
Gnanenthiran et al., "Prospective Meta-Analysis Protocol on Randomised Trials of Renin-Angiotensin System Inhibitors in Patents with COVID-19: An Initiative of the International Society of Hypertension," BMJ Open 11:e043625 (2021), 7 pages.
Ito et al., "Chemopreventive Effects of Angiotensin II Receptor Type 2 Agonist on Prostate Carcinogensesis by the Down-Regulation of the Androgen Receptor," Oncotarget 9(17):13859-13869 (2018).
Tipnis et al., "A Human Homolog of Angiotensin-Converting Enzyme," J. Biol. Chem. 275(43):33238-33243 (2000).
Zhao et al., "Single-Cell RNA Expression Profiling of ACE2, the Receptor of SARS-CoV-2," bioRxiv, doi: https://doi.org/10.1101/2020.01.26.919985 (2020), 15 pages.
Bruce et al., "Selective Activation of Angiotensin AT2 Receptors Attenuates Progression of Pulmonary Hypertension and Inhibits Cardiopulmonary Fibrosis," Br. J. Pharmacol. 172:2219-2231 (2015).
Cui et al., "AGTR2, One Possible Novel Key Gene for the Entry of 2019-nCoV Into Human Cells," Preprints 2020, https://doi:10.20944/preprints202002.0194.v1, 11 pages.
Czick et al., "COVID's Razor: RAS Imbalance, the Common Denominator Across Disparate, Unexpected Aspects of COVID-19," Diabetes, Metabolic Syndrome and Obesity 13:3169-3192 (2020).

(Continued)

*Primary Examiner* — Savitha M Rao
*Assistant Examiner* — Gregg Polansky
(74) *Attorney, Agent, or Firm* — Troutman Pepper Hamilton Sanders LLP (Rochester)

(57) ABSTRACT

There is provided N-butyloxycarbonyl-3-(4-imidazol-1-yl-methylphenyl)-5-isobutylthiophene-2-sulfonamide, or a pharmaceutically-acceptable salt thereof, for use in a method of treatment of respiratory virus-induced tissue damage. Such damage may be caused by coronaviruses, including severe acute respiratory syndrome coronavirus and severe acute respiratory syndrome coronavirus. N-Butyloxycarbonyl-3-(4-imidazol-1-ylmethylphenyl)-5-iso-butyl-thiophene-2-sulfonamide alleviate symptoms of diseases caused by those viruses (including coronavirus disease 2019 or COVID-19), such as cough, dyspnea, pneumonia, respiratory distress, respiratory failure and/or fibrosis of organs such as the lungs, the heart or the kidneys, and may thus prevent respiratory virus-induced morbidity and/or mortality. In particular, it has been found in a clinical study that the proportion of patients with COVID-19 needing oxygen treatment was significantly lower for patients that were administered N-butyloxycarbonyl-3-(4-imidazol-1-ylmeth-ylphenyl)-5-iso-butylthiophene-2-sulfonamide compared to placebo.

14 Claims, No Drawings

(56) References Cited

OTHER PUBLICATIONS

Darrah et al., "AGTR2 Absence or Antagonism Prevents Cystic Fibrosis Pulmonary Mainfestations," Journal of Cystic Fibrosis 18:127-134 (2019).
Fang et al., "Are Patients with Hypertension and Diabetes Mellitus at Increased Risk for COVID-19 Infection?," Lancet Respir. Med. 8:e21 (2020).
Fu et al., "Understanding SARS-CoV-2-Mediated Inflammatory Responses: From Mechanisms to Potential Therapeutic Tools," Virol. Sin. 35:266-272 (2020).
Gabrowska et al., "Soluble E-cadherin: More than a Symptom of Disease," Front. Biosci. (Landmark Ed.) 17:1948-1964 (2014).
George et al., "Pulmonary Fibrosis and COVID-19: The Potential Role for Antifibrotic Therapy," Lancet Respir. Med. 2020, doi.org/10.1016/S2213-2600(20)30225-3 (May 2020).
Gurwitz, David, "Angiotensin Receptor Blockers as Tentative SARS-CoV-2 Therapeutics," Drug Dev Res. 81:537 (2020).
Hoffmann et al., "SARS-CoV-2 Cell Entry Depends on ACE2 and TMPRSS2 and is Blocked by Clinically Proven Protease Inhibitor," Cell 181(271):1-10 (2020).
Hu et al., "E-Cadherin Plays a Role in Hepatitis B Virus Entry through Affecting Glycosylated Sodium-Taurocholate Cotransporting Polypeptide Distribution," Front. Cell. Infect. Microbiol 10(74):1-13 (2020).
Imai et al., "Angiotensin-Converting Enzyme 2 (ACE2) in Disease Pathogenesis," Circ J. 74:405-410 (2010).
Imai et al., "Angiotensin-Converting Enzyme 2 Protects from Severe Acute Lung Failure," Nature 436:112-116 (2005).
Ji et al., "TWIRLS, An Automated Topic-Wise Inference Method Based on Massive Literature, Suggests a Possible Mechanism via ACE2 for the Pathological Changes in the Human Lost After Coronavirus Infection," medRxiv 2020, doi.org/10.1101/2020.02.24.20025437 (Feb. 2020).
Kim et al., "Therapy for Early COIVD-19, A Critical Need," JAMA 324(21) 2149-2150 (2020).
Kuba et al., "A Crucial Role of Angiotensin Converting Enzyme 2 (ACE2) in SARS Coronavirus-Induced Lung Injury," Nat. Med. 11(8):875-879 (2005).
Liu et al., "Research and Development on Therapeutic Agents and Vaccines for COVID-19 and Related Human Coronavirus Diseases," ACS Cent. Sci. 6:315 (2020).
Menk et al., "Angiotensin II Type 2 Receptor Agonist Compound 21 Attenuates Pulmonary Inflammation in a Model of Acute Lung Injury," J. Inflamm. Res. 11:169-178 (2018).
Miura et al., "Host-Pathogen Interactions During Coronavirus Infection of Primary Alveolar Epithelial Cells," J. Leukoc. Biol. 86:1145-1151 (2009).
Patel et al., "Emerging Role of Angiotensin AT2 Receptor in Anti-Inflammation: An Update," Curr. Pharm. Des. 26:1-9 (2020).
Prompetchara et al., "Immune Responses in COVID-19 and Potential Vaccines: Lessons Learned from SARS and MERS Epidemic," Asian Pac. J. Allergy Immunol. 38:1-9 (2020).
Rathinasabapathy et al., "The Selective Angiotensin II Type 2 Receptor Agonist, Compound 21, Attenuates the Progression of Lung Fibrosis and Pulmonary Hypertension in an Experimental Model of Bleomycin-Induced Lung Injury," Front. Physiol. 9(180):1-11 (2018).
Steckelings et al., Correcting the Imbalanced Protective RAS in COVID-19 with Angiotensin AT2-Receptor Agonists Clinical Science 134:2987-3006 (2020).
Struck et al., "A Hexapeptide of the Receptor-Binding Domain of SARS Corona Virus Spike Protein Blocks Viral Entry into Host Cells Via the Human Receptor ACE2," Antiviral Research 94:288-296 (2012).
Unger et al., "The Protective Arm of the Renin-Angiotensin System, Fundamental Aspects and Therapeutic Implications," Eds. Elsevier (London) (2015).
UKIPO Search report for GB 2004209.9, dated Aug. 28, 2020, 5 pages.
Verdonk et al., " Angiotensin II Type 2 Receptor Agonists: Where should they be Applied?," Expert Opin. Investig. Drugs 21(4):501-513 (2012).
Vicore Pharma Press Release "C21 has a Strong Impact on Several Markers in an in vitro Study for Pulmonary Fibrosis," dated Mar. 8, 2017, 2 pages.
Wagenaar et al., "Agonists of MAS Oncogene and Angiotensin II Type 2 Receptors Attenuate Cardiopulmonary Disease in Rats with Neonatal Hyperoxia-Induced Lung Injury," Am. J. Physiol. Lung Cell Mol. Physiol. 305:L341-L351 (2013).
Walls et al., "Structure, Function, and Antigenicity of the SARS-CoV-2 Spike Glycoprotein," Cell 181:1-12 (2020).
Waseda et al., "Angiotensin II type 2 Receptor Antagonist Reduces Bleomycin-Induced Pulmonary Fibrosis in Mice," Respiratory Research 9(43):1-9 (2008).
Wu, "Compensation of ACE2 Function for Possible Clinical Management of 2019-nCoV-Induced Acute Lung Injury," Virol. Sin. 35:256-259 (2020).
Zhang et al., "Angiotensin-Converting Enzyme 2 (ACE2) as a SARS-CoV-2 Receptor: Molecular Mechanisms and Potential Therapeutic Target," Intensive Care Med. 46:586-591 (2020).
Zhou et al., "A Pneumonia Outbreak Associated with a New Coronavirus of Probable Bat Origin," Nature 579:270-290 (2020).
Zhu et al., "Activation of Angiotensin II Type 2 Receptor Suppresses TNF-α-induced ICAM-1 via NF-KB: Possible role at ACE2," Am. J. Physiol. Heart Circ. Physiol. 309:H827-H837 (2015).
Mei et al., "Activation of Angiotensin II Type-2 Receptor Protects Against Cigarette Smoke-induced COPD," Pharmacol. Res. 161:105223 (2020).
Wang et al., "Renin-angiotensin-system, a Potential Pharmacological Candidate, in Acute Respiratory Distress Syndrome During Mechanical Ventilation," Pulm. Pharmacol. Ther. 58:101833 (2019).
Uhal et al., "Regulation of Alveolar Epithelial Cell Survival by the ACE-2/angiotensin 1-7/Mas axis," Am J Physiol Lung Cell Mol Physiol. 301(3):L269-74 (2011).
Zhang et al., "ACE-2/ANG1-7 Ameliorates ER Stress-induced Apoptosis in Seawater Aspiration-induced Acute Lung Injury," Am J Physiol Lung Cell Mol Physiol. 315(6):L1015-L1027 (2018).

\* cited by examiner

USE OF ANGIOTENSIN II TYPE 2 RECEPTOR AGONIST

This application claims the priority benefit of GB 2004209.9, filed Mar. 23, 2020, and GB 2009574.1, filed Jun. 23, 2020.

FIELD OF THE INVENTION

This invention relates to the new use of a known compound.

BACKGROUND AND PRIOR ART

A virus is a very small organism comprising genetic material (DNA or RNA) that is capable of infecting a biological organism. A virus invades and attaches itself to a living cell, after which it multiplies to produce more virus particles (virions), which attach to and enter susceptible cells.

A virus may either kill a cell or alter its functions leading to the infection of other cells. This will then generally lead to what is termed as a viral disease (or a viral infection).

In general, viruses only infect one type of cell, but can be transmitted in various ways, including contact with infected individuals or their bodily secretions, animals (such as arthropods), or inanimate objects. Viruses can also be transmitted by inhalation or swallowing.

Following viral infection, an organism's immune defence system is triggered. White blood cells like lymphocytes and monocytes attempt to attack and destroy the invasive virus. This is part of the body's immune response. The immune response can often lead a patient feeling unwell or fatigued. If a patient's immune system is compromised, or not effective enough to prevent the spread of a virus, this can lead to severe illness and, in some instances, morbidity and/or death.

Indeed, there are many different types of viruses that can seriously affect lung function and cause respiratory illnesses. Common respiratory viruses include corona virus (usually contracted in general usage to 'coronavirus', as used hereinafter), influenza virus, respiratory syncytial virus, parainfluenza virus, adenovirus, rhinovirus, human metapneumovirus and enterovirus.

Coronaviruses are a group of related viruses that cause diseases in mammals and birds. There are 7 presently-known strains of human coronaviruses:

severe acute respiratory syndrome coronavirus (SARS-CoV),
severe acute respiratory syndrome coronavirus 2 (SARS-CoV-2, previously known as '2019-nCoV' or 'novel coronavirus 2019'), which is the virus that causes coronavirus disease 2019 (COVID-19), of which there are at least two subtypes (L and S),
human coronavirus 229E (HCoV-229E, human coronavirus OC43 (HCoV-OC43),
human coronavirus NL63 (HCoV-NL63 or New Haven coronavirus),
human coronavirus HKU1,
Middle East respiratory syndrome-related coronavirus (MERS-CoV), previously known as novel coronavirus 2012, and
Human coronavirus Erasmus Medical Center/2012 (HCoV-EMC/2012).

In humans, coronaviruses cause respiratory tract infections that are typically mild, but some forms such as SARS-CoV and SARS-CoV-2 can be lethal, which is thought to be due to uncontrolled aggressive deleterious pulmonary inflammation and cellular apoptosis (Fu et al, Virol. Sin., 35, 266 (2020)).

Alveolar epithelial cells are an important target for coronavirus infection in the lungs (Miura and Holmes, J. Leukoc. Biol., 86, 1145 (2009)).

Angiotensin converting enzyme (ACE) is a central component of the renin-angiotensin system that converts angiotensin I to the vasoconstrictor angiotensin II (Ang II) known to increase blood pressure. Consequently, ACE inhibiting drugs are widely used for treatment of cardiovascular diseases, in particular hypertension.

Angiotensin converting enzyme 2 (ACE2) is a peptidase that catalyses the conversion of angiotensin I to the nonapeptide angiotensin[1-9] and the conversion of angiotensin II to the heptapeptide angiotensin[1-7]. In human lung tissue, 83% of ACE2-expressing cells have been reported to be alveolar epithelial cells (Zhang et al, Intensive Care Med., 46, 586 (2020)). ACE2 is not sensitive to the ACE inhibitor drugs used to treat hypertension.

The angiotensin II receptor type 1 receptor (AT1R) is a well characterized angiotensin receptor. It mediates Ang II-induced vasoconstriction and regulates aldosterone secretion and thereby controls blood pressure. AT1R blockers (ARBs) are drugs use for treatment of e.g. hypertension and diabetic nephropathy.

Both SARS-CoV and SARS-CoV-2 viruses are known to bind to and enter their target cells through ACE2 (see e.g. Zhang et al, supra and Zhou et al, Nature, 579, 270 (2020)).

As recently summarized by Fang et al in Lancet Respir. Med., 8, e21 (2020), the most distinctive comorbidities of patients with COVID-19 are diabetes and hypertension. As mentioned above, the latter comorbidities are often treated with ACE inhibitors and/or ARBs.

The expression of ACE2 is substantially increased in patients who are treated with ACE inhibitors and/or ARBs, which would be expected to facilitate infection with SARS viruses. Accordingly, Fang et al, supra, suggested that treatment of e.g. diabetic and hypertensive patients with ACE2-stimulating drugs may increase the risk of developing severe and fatal SARS infections such as COVID-19.

The angiotensin II type 2 receptor (AT2R or AGTR2) mediates anti-inflammatory, anti-fibrotic, antiproliferative and vasodilatory activities when activated by an AT2R agonist (see e.g. Verdonk et al, Expert Opin. Investig. Drugs 21, 501 (2012).

It was recently reported in a paper by Cui et al, Preprints (2020), https://doi:10.20944/preprints202002.0194.v1 that the AT2R may, in a similar fashion to ACE2, contribute to entry of 2019-nCoV into human cells.

Imai et al (Nature, 436, 112 (2005)) reported that an AT2R blocker had no effect on disease progression following non-viral stimulation of lung injury, suggesting that the apparent protective role of AT2R was unrelated to any AT2R agonistic activation. It has also been demonstrated in models of cystic fibrosis (CF) that blocking (rather than stimulating) the AT2R prevents CF manifestation, i.e. reduced ATR2 signaling is beneficial to CF lung function (Darrah et al, Journal of Cystic Fibrosis, 18, 127 (2019). Likewise, blocking of the AT2R has also been shown to significantly reduce chemically-induced pulmonary inflammation (Waseda et al, Respiratory Research, 9, 43 (2008)).

International patent application WO 2002/096883 describes the preparation of imidazolyl, triazolyl, and tetrazolyl thiophene sulfonamides and derivatives thereof as angiotensin II receptor agonists. Of the compounds described in that document (as Example 1) is Compound 21

(N-butyloxycarbonyl-3-(4-imidazol-1-ylmethylphenyl)-5-isobutylthiophene-2-sulfonamide; hereafter '021'. C21 was selected for clinical development from a group of about 20 related analogues as a selective AT2 agonist. It is now in clinical development for treatment of AT2 related disorders, including idiopathic pulmonary fibrosis (IPF) (see, for example, international patent application WO 2016/139475).

C21 has been shown to increase the expression of both AT2R itself and ACE2, in particular in inflamed lung tissue (Bruce et al, *Br. J. Pharmacol.*, 172, 2219 (2015)). Moreover, C21 has been found not to improve pulmonary gas exchange or have other relevant beneficial clinical effects in a model of acute lung injury (Menk et al, *J. Inflamm. Res.*, 11, 169 (2018)).

Surprisingly, we have found that C21 has beneficial effects on human airway epithelium, and protects against SARS virus-induced pulmonary epithelial damage and dysfunction in patients in a clinical setting. In particular, as described below, in a double-blind placebo-controlled clinical study carried out in COVID-19 patients, the need for oxygen treatment was significantly lower in patients that were administered C21 compared to placebo. The number of patients needing mechanical ventilation was also found to be reduced in the C21 group.

DISCLOSURE OF THE INVENTION

According to the invention, there is provided C21 or a pharmaceutically-acceptable salt thereof for use in a method of treatment of respiratory virus-induced tissue damage.

Tissue damage includes injury and/or dysfunction of relevant tissues. Relevant tissues include (e.g. mucosal) tissues of the respiratory tract, and especially those of the lung. Relevant tissue thus includes the respiratory epithelium, which moistens the airways and protects against invasion of pathogens such as viruses.

Respiratory viruses that may be mentioned include influenza viruses and, more particularly, coronaviruses such as those mentioned hereinbefore, including SARS coronaviruses, such as SARS-CoV and, especially, SARS-CoV-2.

By 'treatment' of tissue damage, we include that C21 and salts thereof may not only have a beneficial effect on tissue damage in the respiratory tract that has been caused by such a virus, but that it may also prevent and/or mitigate the damage that would otherwise have been caused by that virus in the respiratory tract, which occurs when the relevant virus enters e.g. epithelial cells in the respiratory tract.

For the avoidance of doubt therefore, 'treatment' of tissue damage includes the therapeutic, symptomatic and palliative treatment of such damage, as well as, in principle, the prophylaxis of such damage, or during the diagnostic workup of such damage (i.e. if it is suspected). More importantly, C21 and salts thereof may abrogate or prevent the development of diseases that are caused by such tissue damage and/or the symptoms of such damage or diseases.

In this respect, C21 and salts thereof may treat, and/or arrest the progress of, diseases that are being, or have been, caused by respiratory viruses (i.e. diseases such as acute lung injury (ALI), acute respiratory distress syndrome (ARDS), particularly SARS and, more particularly, COVID-19). C21 and salts thereof may also treat and/or prevent the damage that is being, or has been, caused by such viruses, which includes treating and/or preventing the symptoms of such respiratory diseases, which symptoms include cough, dyspnea, respiratory distress (as manifest by e.g. the need for supplementary oxygen and/or mechanical ventilation) and/or respiratory failure, as well as pneumonia, and fibrosis in the lungs and other organs, such as the heart and kidneys. Such fibrosis is known to be a particular problem in many COVID-19 patients, and may result from one or more of a number of factors, including inflammation. In this respect, C21 and salts thereof may prevent or arrest the progress of respiratory virus-induced morbidity and/or mortality, and C21 may treat, and/or arrest the development of any of the chronic symptoms identified above.

Salts of C21 that may be mentioned include pharmaceutically-acceptable acid addition salts and base addition salts. Such salts may be formed by conventional means, for example by reaction of free compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin. Preferred salts of C21 include acid addition salts, such as HCl salts, alkaline earth salts, such as magnesium and calcium salts, and alkali metal salts, such as potassium or, preferably, sodium salts.

Although C21 and salts thereof may possess biological activity as such, certain pharmaceutically-acceptable (e.g. 'protected') derivatives of C21 may exist or be prepared which may not possess such activity, but may be administered and thereafter be metabolised in the body to form C21. Such compounds (which may possess some biological activity, provided that such activity is appreciably lower than that of C21) may therefore be described as 'precursors' or 'prodrugs' of C21.

As used herein, references to precursors or prodrugs will include compounds that form C21, in an experimentally-detectable amount, within a predetermined time, following administration. All precursors and prodrugs of C21 are included within the scope of the invention.

According to a further aspect of the invention there is provided a method of medical treatment of respiratory virus-induced tissue damage as hereinbefore defined, which method comprises administering C21 or a pharmaceutically-acceptable salt thereof to a subject in need of such treatment.

'Subjects' (which may be employed interchangeably herein with 'patients') include avian and, especially, mammalian (particularly human) subjects and/or patients. Human patients include both adult patients as well as paediatric patients, the latter including patients up to about 24 months of age, patients between about 2 to about 12 years of age, and patients between about 12 to about 16 years of age. Patients older than about 16 years of age may be considered adults for purposes of the present invention. These different patient populations may be given different doses of C21, or salt thereof.

It is preferred, in accordance with the invention, that C21 or a pharmaceutically-acceptable salt thereof is administered to adult patients/subjects, more particularly subjects that are over the age of about 20, such as over the age of about 30, including over the age of about 40, more preferably over the age of about 50, especially over the age of about 60, particularly over the age of about 70, and more particularly over the age of about 80.

It is further preferred that C21 or a pharmaceutically-acceptable salt thereof is administered to patients/subjects (whether or not such subjects are in one of the age groups specified above) with one or more of the following underlying medical conditions:

chronic (long-term) respiratory diseases, such as asthma, chronic obstructive pulmonary disease (COPD), emphysema or bronchitis chronic cardiovascular (e.g. heart) disease, such as heart failure, atrial fibrillation or hypertension chronic kidney disease chronic liver disease, such as hepatitis chronic neurological conditions, such as Parkinson's disease, motor neurone disease, multiple sclerosis, a learning disability or cerebral palsy diabetes problems with a patient's spleen—for example, sickle cell disease or if the spleen has been removed a weakened immune system as the result of conditions, such as HIV and AIDS, or medicines such as steroid tablets or chemotherapy obesity (e.g. a body mass index (BMI) of 40 or above)

pregnancy

In accordance with the invention, C21 and pharmaceutically-acceptable salts thereof may be administered locally or systemically, for example orally, intravenously or intraarterially (including by intravascular and other perivascular devices/dosage forms (e.g. stents)), intramuscularly, cutaneously, subcutaneously, transmucosally (e.g. sublingually or buccally), rectally, intravaginally, transdermally, nasally, pulmonarily (e.g. tracheally or bronchially), topically, or by any other parenteral route, in the form of a pharmaceutical preparation comprising the compound(s) in pharmaceutically-acceptable dosage form(s).

Treatment may thus be induced by systemic administration of C21 and pharmaceutically-acceptable salts thereof, for example by way of oral administration (e.g. as described hereinafter), by way of a parenteral route (e.g. by injection), or by way of pulmonary administration, for example as described in international patent application WO 2020/095042 (PCT application number GB2019/053137).

Other modes of delivery of C21 and pharmaceutically-acceptable salts thereof include topical administration. In such a mode of administration, absorption of compound of the invention into systemic circulation may occur, or the compound of the invention may act locally at the site of administration (e.g. the respiratory mucosa).

C21 and pharmaceutically-acceptable salts thereof will generally be administered in the form of one or more formulations in admixture with an (e.g. pharmaceutically-acceptable) adjuvant, diluent or carrier, which may be selected with due regard to the intended route of administration and standard pharmaceutical practice. Acceptable carriers may be chemically inert to the active compounds and may have limited (or preferably no) detrimental side effects or toxicity under the conditions of use. Such carriers may also impart an immediate, or a modified, release of the active ingredient.

Suitable pharmaceutical formulations may be commercially available or may otherwise be prepared according to techniques that are described in the literature, for example, Remington *The Science and Practice of Pharmacy*, 22$^{nd}$ edition, Pharmaceutical Press (2012) and *Martindale—The Complete Drug Reference*, 38$^{th}$ Edition, Pharmaceutical Press (2014) and the documents referred to therein, the relevant disclosures in all of which documents are hereby incorporated by reference.

Otherwise, the preparation of suitable formulations including C21 and pharmaceutically-acceptable salts thereof may be achieved non-inventively by the skilled person using routine techniques.

According to a further aspect of the invention there is provided a pharmaceutical composition comprising C21 or a pharmaceutically-acceptable salt thereof, along with one or more pharmaceutically-acceptable excipient(s), such as an adjuvant, diluent or carrier which composition is packaged and presented for use in a method of treatment of respiratory virus-induced tissue damage.

Administration of active ingredients may be continuous or intermittent.

The mode of administration may also be determined by the timing and frequency of administration, but is also dependent on the severity of that condition, or otherwise on the need for treatment.

The amount of active ingredient in a formulation will depend, and/or may be selected depending, upon the severity of the respiratory virus-induced tissue damage, or the expectation of such severity, as well as on the subject to be treated, but may be determined by the skilled person.

In any event, the practitioner, or other skilled person, will be able to determine routinely the actual dosage, which will be most suitable for an individual subject. Dosages mentioned herein are exemplary of the average case; there can, of course, be individual instances where higher or lower dosage ranges are merited, and such are within the scope of this invention.

In relation to (for example) acute treatment of respiratory virus-induced tissue damage, doses of C21 or salt thereof may be administered between once and four times (e.g. between 1 and 3 times) daily for up to three (e.g. two) months, such as one month, including up to three weeks, e.g. up to one week, such as 4 days or 3 days. Such treatment periods may be repeated as appropriate.

In the case of the development of one or more of the chronic symptoms identified hereinbefore, such as fibrosis of the lungs and other internal organs, treatment with C21 or salt thereof may, in addition to and/or instead of the above-mentioned acute dosing regimens, be continuous and/or as needed/required.

Suitable oral daily doses (calculated as the free base) of C21 in adult subjects (average weight e.g. 70 kg), may be up to about 600 mg, including about 400 mg and about 200 mg, and no lower than about 50 mg.

In any event, the dose administered to a mammal, particularly a human, in the context of the present invention should be sufficient to effect a response in the subject over a reasonable timeframe (e.g. as described herein). One skilled in the art will recognize that the selection of the exact dose and composition and the most appropriate delivery regimen will also be influenced by inter alia the pharmacological properties of the formulation, the physical condition of the recipient, including the age, condition, body weight, sex and response of the subject to be treated, and also the nature, stage and/or severity of the disease, and genetic differences between subjects.

In the uses and methods described herein, C21 and salts thereof may also be combined with one or more therapeutic agents that are useful in the treatment of patients with viral infections and/or the symptoms of diseases caused thereby.

Therapeutic agents that may be used in conjunction with C21 in accordance with the invention include variously-applied standard treatments for viral infections, including antiviral medicines (e.g. oseltamivir, remdesivir, favilavir, simeprevir, daclatasvir, sofosbuvir, ribavirin, umifenovir, lopinavir, ritonavir, teicoplanin, the TMPRSS2 inhibitor, camostat, Actembra (Roche), TZLS-501, AT-100 (rhSP-D), OYA1 (OyaGen9), BPI-002 (BeyondSpring), NP-120 (Ifenprodil; Algernon Pharmaceuticals), Galidesivir (Biocryst Pharma), REGN3048-3051 and Kevzara (SNG001; Synairgen Research), antiinflammatory agents (e.g. NSAIDs, such as ibuprofen, ketorolac, naproxen, and the like), chloroquine, hydroxychloroquine, interferons (e.g. interferon beta, interferon beta-1a), tocilizumab, lenalidomide, pomalidomide and thalidomide), analgesics (e.g. paracetamol or opioids), antitussive agents (e.g. dextromethorphan), vaccinations (e.g. INO-4800 by lnovio Pharmaceuticals and Beijing Advaccine Biotechnology, if available), and/or passive antibody therapy with antibodies from blood of people who have recovered from infection with SARS-CoV or SARS-CoV-2.

Further therapeutic agents that may be mentioned include anti-fibrotics (e.g. nintedanib and, particularly, pirfenidone), vitamins (e.g. vitamin B, C and D) and mucolytics such as acetylcysteine and ambroxol.

Other therapeutic agents that may be used in conjunction with C21 or salts thereof in accordance with the invention include corticosteroids. Corticosteroids include both naturally-occurring corticosteroids and synthetic corticosteroids.

Naturally-occurring corticosteroids that may be mentioned include cortisol (hydrocortisone), aldosterone, corticosterone, cortisone, pregnenolone, progesterone, as well as naturally-occurring precursors and intermediates in corticosteroid biosynthesis, and other derivatives of naturally-occurring corticosteroids, such as 11-deoxycortisol, 21-deoxycortisol, 11-dehydrocorticosterone, 11-deoxycorticosterone, 18-hydroxy-11-deoxycorticosterone, 18-hydroxycorticosterone, 21-deoxycortisone, 11β-hydroxypregnenolone, 11β,17α,21-trihydroxypregnenolone, 17α,21-dihydroxypregnenolone, 17α-hydroxypregnenolone, 21-hydroxypregnenolone, 11-ketoprogesterone, 11β-hydroxyprogesterone, 17α-hydroxyprogesterone and 18-hydroxyprogesterone.

Synthetic corticosteroids that may be mentioned include those of the hydrocortisone-type (Group A), such as cortisone acetate, hydrocortisone aceponate, hydrocortisone acetate, hydrocortisone buteprate, hydrocortisone butyrate, hydrocortisone valerate, tixocortol and tixocortol pivalate, prednisolone, methylprednisolone, prednisone, chloroprednisone, cloprednol, difluprednate, fludrocortisone, fluocinolone, fluperolone, fluprednisolone, loteprednol, prednicarbate and triamcinolone; acetonides and related substances (Group B), such as amcinonide, budesonide, desonide, fluocinolone cetonide, fluocinonide, halcinonide, triamcinolone acetonide, ciclesonide, deflazacort, formocortal, fludroxycortide, flunisolide and fluocinolone acetonide, those of the (beta)methasone-type (Group C), such as beclomethasone, betamethasone, betamethasone dipropionate and betamethasone valerate, dexamethasone, fluocortolone, halometasone, mometasone and mometasone furoate, alclometasone and alclometasone dipropionate, clobetasol and clobetasol propionate, clobetasone and clobetasone butyrate, clocortolone, desoximetasone, diflorasone, difluocortolone, fluclorolone, flumetasone, fluocortin, fluprednidene and fluprednidene acetate, fluticasone, fluticasone furoate and fluticasone propionate, meprednisone, paramethasone, prednylidene, rimexolone and ulobetasol; those of the progesterone-type, such as flugestone, fluorometholone, medrysone and prebediolone acetate, and progesterone derivatives (progestins), such as chlormadinone acetate, cyproterone acetate, medrogestone, medroxyprogesterone acetate, megestrol acetate and segesterone acetate; as well as other corticosteroids, such as cortivazol and 6-methyl-1β,17β-dihydroxy-17α-(1-propynyl)androsta-1,4,6-trien-3-one.

Preferred corticosteroids, include cortisone, prednisone, prednisolone, methylprednisolone and, especially, dexamethasone.

Further, therapeutic agents that may be used in conjunction with C21 or salts thereof include H2 receptor blockers, anticoagulants, anti-platelet drugs, as well as statins, antimicrobial agents and anti-allergic/anti-asthmatic drugs.

H2 receptor blockers that may be mentioned include famotidine. Anticoagulants that may be mentioned include heparin and low-molecular-weight heparins (e.g. bemiparin, nadroparin, reviparin, enoxaparin, parnaparin, certoparin, dalteparin, tinzaparin); directly acting oral anticoagulants (e.g. dabigatran, argatroban, rivaroxaban, apixaban, edoxaban, betrixaban, darexaban, otamixaban, letaxaban, eribaxaban, hirudin, lepirudin and bivalirudin); coumarin type vitamin K antagonists (e.g. coumarin, acenocoumarol, phenprocoumon, atromentin and phenindione) and synthetic pentasaccharide inhibitors of factor Xa (e.g. fondaparinux, idraparinux and idrabiotaparinux). Anti-platelet drugs that may be mentioned include irreversible cyclooxygenase inhibitors (e.g. aspirin and triflusal); adenosine diphosphate receptor inhibitors (e.g. cangrelor, clopidogrel, prasugrel, ticagrelor and ticlopidine); phosphodiesterase inhibitors (e.g. cilostazol); protease-activated receptor-1 antagonists (e.g. vorapaxar); glycoprotein IIB/IIIA inhibitors (e.g. abciximab, eptifibatide and tirofiban); adenosine reuptake inhibitors (e.g. dipyridamole); and thromboxane inhibitors (e.g. terutroban, ramatroban, seratrodast and picotamide). Statins that may be mentioned include atorvastatin, simvastatin and rosuvastatin. Antimicrobial agents that may be mentioned include azithromycin, ceftriaxone, cefuroxime, doxycycline, fluconazole, piperacillin, tazobactam and teicoplanin. Anti-allergic/anti-asthmatic drugs that may be mentioned include chlorphenamine, levocetirizine and montelukast.

Subjects may thus also (and/or may be already) be receiving one or more of any of the other therapeutic agents mentioned above, by which we mean receiving a prescribed dose of one or more of those other therapeutic agents, prior to, in addition to, and/or following, treatment with C21/salt.

When C21/salts are 'combined' with such other therapeutic agents, the active ingredients may be administered together in the same formulation, or administered separately (simultaneously or sequentially) in different formulations.

Such combination products provide for the administration of C21/salt in conjunction with the other therapeutic agent, and may thus be presented either as separate formulations, wherein at least one of those formulations comprises C21/salt, and at least one comprises the other therapeutic agent, or may be presented (i.e. formulated) as a combined preparation (i.e. presented as a single formulation including C21/salt and the other therapeutic agent).

Thus, there is further provided:

(1) a pharmaceutical formulation including C21 or a pharmaceutically-acceptable salt thereof; a therapeutic agent that is useful in the treatment of a viral infection; and a pharmaceutically-acceptable adjuvant, diluent or carrier (which formulation is hereinafter referred to as a 'combined preparation'); and (2) a kit of parts comprising components:

(A) a pharmaceutical formulation including C21 or a pharmaceutically-acceptable salt thereof in admixture with a pharmaceutically-acceptable adjuvant, diluent or carrier; and (B) a pharmaceutical formulation including a therapeutic agent that is useful in the treatment of a viral infection, in admixture with a pharmaceutically-acceptable adjuvant, diluent or carrier, which components (A) and (B) are each provided in a form that is suitable for administration in conjunction with the other.

Such combined preparations and kits of parts may thus be used in the treatment of respiratory virus-induced tissue damage.

According to a further aspect of the invention, there is provided a method of making a kit of parts as defined above, which method comprises bringing component (A), as defined above, into association with a component (B), as defined above, thus rendering the two components suitable for administration in conjunction with each other.

By bringing the two components 'into association with' each other, we include that components (A) and (B) of the kit of parts may be:

(i) provided as separate formulations (i.e. independently of one another), which are subsequently brought together for use in conjunction with each other in combination treatment; or (ii) packaged and presented together as separate components of a 'combination pack' for use in conjunction with each other in combination treatment.

Thus, there is further provided a kit of parts comprising:
(I) one of components (A) and (B) as defined herein; together with
(II) instructions to use that component in conjunction with the other of the two components.

The kits of parts described herein may comprise more than one formulation including an appropriate quantity/dose of C21/salt, and/or more than one formulation including an appropriate quantity/dose of the other therapeutic agent, in order to provide for repeat dosing. If more than one formulation (comprising either active compound) is present, such formulations may be the same, or may be different in terms of the dose of either compound, chemical composition(s) and/or physical form(s).

With respect to the kits of parts as described herein, by 'administration in conjunction with', we include that respective formulations comprising a C21/salt and other therapeutic agent are administered, sequentially, separately and/or simultaneously, over the course of treatment of the condition.

Thus, in respect of the combination product according to the invention, the term 'administration in conjunction with' includes that the two components of the combination product (C21 and other agent) are administered (optionally repeatedly), either together, or sufficiently closely in time, to enable a beneficial effect for the subject, that is greater, over the course of the treatment of the condition, than if either a formulation comprising C21/salt, or a formulation comprising the other therapeutic agent that is useful in the treatment of a viral infection, are administered (optionally repeatedly) alone, in the absence of the other component, over the same course of treatment. Determination of whether a combination provides a greater beneficial effect in respect of, and over the course of treatment will depend upon the condition to be treated and/or its severity, but may be achieved routinely by the skilled person.

Further, in the context of a kit of parts according to the invention, the term 'in conjunction with' includes that one or other of the two formulations may be administered (optionally repeatedly) prior to, after, and/or at the same time as, administration of the other component. When used in this context, the terms 'administered simultaneously' and 'administered at the same time as' include that individual doses of C21 and other therapeutic agent are administered within 48 hours (e.g. 24 hours) of each other.

In a further aspect of the invention, there is provided a process for the preparation of a combined preparation as hereinbefore defined, which process comprises bringing into association C21 or a pharmaceutically-acceptable salt thereof, a therapeutic agent that is useful in the treatment of a viral infection, and at least one pharmaceutically-acceptable excipient.

Wherever the word 'about' is employed herein, for example in the context of amounts, such as concentrations and/or doses of active ingredients, ages, etc., it will be appreciated that such variables are approximate and as such may vary by ±10%, for example ±5% and preferably ±2% (e.g. ±1%) from the numbers specified herein. In this respect, the term 'about 10%' means e.g. ±10% about the number 10, i.e. between 9% and 11%.

C21 has the advantage that it is more effective, has considerably less side effects, and/or is much safer, than current treatments of respiratory viral infections, and the (e.g. serious) diseases that are or may be caused thereby, such as those mentioned hereinbefore.

The uses and methods described herein may also have the advantage that, in the treatment of respiratory virus-induced tissue damage, they may be more convenient for the subject than, be more efficacious than, be less toxic than, have a broader range of activity than, be more potent than, produce fewer side effects than, or that it/they may have other useful pharmacological properties over, similar methods (treatments) known in the prior art, whether for use in the treatment of respiratory virus-induced tissue damage, viral infections generally, or otherwise.

The invention is illustrated by the following examples.

EXAMPLE 1

Effect of C21 in In Vitro Human Airway Epithelial Cell Assay

The effect of C21 on E-cadherin expression was studied using the human disease model BioMAP® platform (fibrosis panel) with ELISA-based protein biomarker detection in a human small airway epithelial cell plus lung fibroblast (SAEMyoF) assay (a service provided by Eurofins DiscoverX Corporation, Fremont, Calif., USA). E-cadherin is a calcium-dependent epithelial cell adhesion molecule and has been suggested to contribute to disease progression (Gabrowska and Day, *Front. Biosci.* (*Landmark Ed.*), 17, 1948 (2014)), and also to play a critical role in viral infection at the level of host cell binding and viral entry into cells (see Hu et al, *Front. Cell. Infect. Microbiol.*, 10, Article 74 (2020), https://doi.org/10.3389/fcimb.2020.00074).

It was found that C21 dose-dependently reduced E-cadherin levels. The relative expression level of E-cadherin (expressed as Log ratio C21/Vehicle control) was −0.0476 with 10 µM of C21. Lower concentrations of C21 (0.37, 1.1 and 3.3 µM) did not reduce E-cadherin.

EXAMPLE 2

In Vitro Cell Assay I

SARS virus cellular entry and/or replication is studied in vitro using appropriate methods described in the scientific literature, for example as described in Struck et al, *Antioviral Research*, 94, 288 (2012), Walls et al, *Cell*, 180, 1 (2020) and/or Zhou et al, *Nature*, 579, 270 (2020). Other relevant/equivalent cell types (including alveolar epithelial type II (ATII) cells) and methods for measuring viral cellular entry and/or replication may also be used. Prior to and/or during exposure of cells to different amounts of virus, the cells are incubated with different concentration (e.g. from 0.1 nM to 1 mM) of C21 for different periods of time.

EXAMPLE 3

In Vitro Cell Assay II

Experiments are performed by FibroFind Limited, Gateshead, United Kingdom.

Precision Cut Lung Slices (PCLuS) from explanted diseased (with idiopathic pulmonary fibrosis) human lung tissue are used. PCLuS are prepared from explanted human lung tissue collected at the time of lung transplantation. PCLuS are rested for 48 hours to allow the post-slicing stress period to elapse before experiments begin. PCLuS are cultured in the presence or absence of Alk5 inhibitor (10 µM) as a positive control. In addition, in separate wells, PCLuS are cultured in the presence of C21 at different concentrations (0.01, 0.1, 1 and/or 10 µM).

PCLuS culture supernatant (n=4-6 per group) is collected daily and snap frozen for quantification of levels of epithelial cell damage biomarkers (MMP7, GDF15, CA125, CEA, CA19-9, cytokeratin 18 and/or CYFRA-21-1) at 48, 96 and 144 hours using R&D Duoset ELISA kits and/or sandwich ELISA (from e.g. Abcam and/or RayBioTech).

EXAMPLE 4

Clinical Trial Evaluating Safety and Efficacy of C21 in Patients with SARS-CoV-2 Virus Infection (I)

This is a clinical study evaluating the safety and effectiveness of C21 (100-400 mg, including 200 mg, daily).

The key objectives/endpoints of the study are to evaluate the safety and efficacy of C21 in participants with infection with SARS-CoV-2 virus.

Evaluation of efficacy of C21 is determined by determining inter alia:
- improvement in signs, symptoms, quality of life, manifestations and/or complications related to the disease, including fever, pulmonary and/or cardiac function, blood oxygen tension/hypoxia, cough, shortness of breath, multiple organ dysfunction syndrome (MODS), acute respiratory distress syndrome (ARDS), secondary pneumonia by other microorganisms and/or patient and/or clinician reported quality of life (QoL) outcome measures;
- duration of hospital stay;
- need for invasive and/or non-invasive ventilation;
- surrogate markers of inflammation, immune response and/or infection, including radiography, ultra-sound, magnetic resonance imaging (MRI), computed tomography (CT) and/or other imaging modalities;
- composite measures and/or ordinal scales that determine disease severity, for example time to clinical recovery and/or sequential organ failure assessment score (SOFA score);
- viral titers and/or seroconversion;
- morbidity and/or mortality;
- and/or effects on relevant biomarkers, including those of epithelial damage/dysfunction (including MMP7, GDF15, CA125, CEA, CA19-9, cytokeratin 18 CCL18, Surfactant Protein-D and/or CYFRA-21-1), and biomarkers of systemic inflammation, immune response and/or infection, including C reactive protein, interleukin-6, tumor necrosis factor, blood leukocytes and/or antibodies.

Subjects for inclusion in the trial are those diagnosed with SARS-CoV-2 infection confirmed by polymerase chain reaction (PCR) test (or another relevant/equivalent test for this purpose), subjects that have been exposed to SARS-CoV-2, and/or symptomatic subjects that are suspected to have a SARS-CoV-2 infection.

Other inclusion criteria are defined in detail by the sponsor together with the investigators. Similarly, exclusion criteria are defined in detail by the sponsor together with the investigators, and may include subjects that inter alia:
- have participated in any other clinical trial of an experimental treatment for SARS-CoV-2 infection or COVID 19 disease;
- require mechanical ventilation at the time of screening;
- have a BMI of >32 or <18;
- have a concurrent respiratory disease such as asthma, COPD or an interstitial lung disease;
- have used medications known to chronically alter drug absorption or elimination processes within 30 days before the first dose administration;
- have participated in a clinical study involving administration of an investigational drug or a marketed drug within the past 3 months;
- have ailments that, in the opinion of the investigator, would interfere with the evaluation of the results or constitute a health risk for the study subject;
- have serum hepatitis or are carriers of the hepatitis B surface antigen (HBsAg) or hepatitis C antibody;
- have had positive result to the test for HIV antigens and/or antibodies;
- are current or previous (<6 months) smokers;
- have a susceptibility to severe allergic reactions;
- have donated blood or suffered a loss of a significant amount of blood within 2 months prior to the first study treatment administration;
- have had a positive urine drug screen result at screening or randomly thereafter;
- are pregnant women, or are women with childbearing potential not using regular contraceptives;
- are men that are unwilling to use a condom for contraception when having sexual intercourse with a fertile woman, during the entire study and at least for 7 days after the last IMP intake.

Subjects are also asked to abstain from drinking alcoholic beverages for 12 hours before screening and during the study.

Instructions are given to take IMP fasted in the morning and 1 hour before intake of any food. The evening dose is ideally taken 2-4 hours of food fasting before intake and 1 hour after taking the drug.

The following medications are avoided in conjunction with C21 treatment:
- CYP3A4 inducers (e.g. rifampicin, phenytoin, St John's Wort)
- CYP3A4 inhibitors (e.g. clarithromycin, ketoconazole, nefazodone, itraconazole, ritonavir)
- medicines that are substrates of CYP1A2, CYP3A4 or CYP2C9 with a narrow therapeutic range
- BCRP sensitive substrates (e.g. sulphasalazine, rosuvastatin)
- H2 receptor antagonists and proton pump inhibitors

EXAMPLE 5

Compassionate Uses

As an alternative to a clinical trial, the safety and efficacy of C21 (using similar criteria to those mentioned in Example 4 above), is determined by conducting early access to C21 on a compassionate-use basis such as a named (individual) patient program and/or an early access program on a cohort basis.

EXAMPLE 6

Clinical Trial Evaluating Safety and Efficacy of C21 in Patients with SARS-CoV-2 Virus Infection (II)
Protocol This was a randomised, double-blind, placebo-controlled, phase 2 trial conducted at multiple sites in India investigating the safety and efficacy of C21 in hospitalised subjects with COVID-19 infection not requiring mechanical ventilation.

The primary objective of the study was to investigate the efficacy of C21 200 mg daily dose (100 mg b.i.d.) on COVID-19 infection not requiring mechanical invasive or non-invasive ventilation. The secondary objectives were to evaluate the effect on inflammation and the safety profile of C21 at the same daily dose. Exploratory objectives include the investigation of a range of laboratory parameters as potential biomarkers of inflammation and viral load, following oral administration of that daily dose.

The primary endpoint of the trial was the change from baseline in measured values of C-reactive protein (CRP) after treatment (initial symptoms are not necessarily predictive of disease severity).

Secondary endpoints included changes from baseline in:
body temperature
IL-6
IL-10
TNF
CA125
Ferritin
as well as
1) the number of subjects not in need of oxygen supply
2) the number of subjects not in need of mechanical invasive or non-invasive ventilation
3) the time until subjects were in need of mechanical invasive or non-invasive ventilation
4) the time subjects were on oxygen supply (for those not needing mechanical invasive or non-invasive ventilation)
5) numbers and severity of adverse events.

Blood samples were saved for potential future analyses of biomarkers reflecting inflammation and lung injury.

The trial was conducted on top of local standard of care for 7 days on approximately 100 subjects from multiple sites that have with COVID-19 infection. Subjects were randomised 1:1 to receive either standard of care+C21 (ca. N=50) or standard of care+placebo (ca. N=55).

All subjects were followed-up between 7 and 10 days after receiving the last investigational medicinal product (IMP) dose (visit or phone call, if recovering at home).

Inclusion criteria included the following:
1) Written informed consent, consistent with ICH GCP R2 and local laws, obtained before the initiation of any trial related procedure.
2) Diagnosis of coronavirus (SARS-CoV-2) infection, confirmed by polymerase chain reaction (PCR) test within 4 days of Visit 1 with signs of an acute respiratory infection.
3) Age between 18 and 70 years inclusive.
4) CRP between 50 and 150 mg/L inclusive.
5) Admitted to a hospital or controlled facility (home quarantine was not deemed sufficient).
6) In the opinion of the Investigator, the subject was able to comply with the requirements of the protocol.

Exclusion criteria at the outset include one or more of the following:
1) Any previous experimental treatment for COVID-19.
2) Need for mechanical invasive or non-invasive ventilation.
3) Concurrent respiratory disease such as chronic obstructive pulmonary disease, idiopathic pulmonary disease (IPF) and/or intermittent, persistent or more severe asthma requiring daily therapy or any subjects that have had an asthma flare requiring corticosteroids in the 4 weeks (28 days) prior to COVID-19 diagnosis.
4) Participation in any other interventional trial within 3 months prior to Visit 1.
5) Any of the following findings at Visit 1:
positive results for hepatitis B surface antigen (HBsAg), hepatitis C virus antibody (HCVAb) or human immunodeficiency virus 1+2 antigen/antibody (HIV 1+2 Ag/Ab); or
positive pregnancy test.
6) Clinically significant abnormal laboratory value at Visit 1 indicating a potential risk for the subject if enrolled in the trial as evaluated by the investigator.
7) Concurrent serious medical condition with special attention to cardiac or ophthalmic conditions (e.g. contraindications to cataract surgery), which in the opinion of the Investigator makes the subject inappropriate for this trial.
8) Malignancy within the past 3 years with the exception of in situ removal of basal cell carcinoma and cervical intraepithelial neoplasia grade I.
9) Treatment with any of the medications listed below within 1 week prior to Visit 1:
strong Cytochrome p450 (CYP) 3A4 inducers (e.g. rifampicin, phenytoin, St. John's Wort, phenobarbital, rifabutin, carbamazepine, anti HIV drugs, barbituates); or
warfarin.
10) Pregnant or breast-feeding female subjects.
11) Female subjects of childbearing potential not willing to use prescribed contraceptive methods.
12) Male subjects not willing to use prescribed contraceptive methods.
13) Subjects known or suspected of not being able to comply with the trial protocol (e.g. due to alcoholism, drug dependency or psychological disorder).

A subject was withdrawn from IMP if any of the following occurred:
Need for mechanical invasive or non-invasive ventilation
Discharge from the hospital/controlled facility
Major protocol deviations as defined by Sponsor.
Sponsor decision to stop the subject's participation in the trial; reasons included medical, safety, or regulatory issues, or other reasons consistent with applicable laws, regulations, and GCP.
It was the wish of the subject for any reason
The Investigator judged it necessary for medical reasons
Adverse events such as:
Serious cardiovascular complications such as severe peripheral oedema or significant bradycardia indicating a potential risk for the subject as evaluated by the Investigator Moderate to severe skin rashes as judged by the Investigator e.g. Stevens-Johnson syndrome and toxic epidermal necrolysis Pregnancy A subject was withdrawn from the trial if any of the following occurred:

Enrolment in other clinical studies involving investigational products or enrolment in other types of clinical research judged not to be scientifically or medically compatible with this trial.

Disallowed treatment during the trial period

It was the wish of the subject for any reason

The Investigator judged it necessary for medical reasons

Adverse events

Lost to follow-up

IMP was delivered as 50 mg capsules (HPMC hard capsules) with a final composition as set out in Table 1 below.

TABLE 1

| Ingredient | Composition | |
|---|---|---|
| | mg/capsule | % w/w |
| C21 sodium salt | 52.8 | 20.24 |
| mannitol (Pearlitol 50C) | 203.38 | 77.93 |
| colloidal silicon dioxide (Aerosil 200) | 2.14 | 0.82 |
| magnesium stearate (Ligamed MF-2-V) | 2.61 | 1.00 |

Capsules were packed in plastic container units with 28 capsules in each. Each unit contained either C21 or matching placebo (the same composition except that C21 was replaced with mannitol.

At the trial site, IMP was stored separately from normal clinic stocks in a securely locked area only accessible to authorised trial personnel. Labeling of the IMP was in the relevant local language (English) and was done in compliance with GMP (GMP 2003) and local regulatory requirements.

IMP was administered twice daily to the subjects for 7 days as follows:

Morning dose: Two 50 mg capsules (100 mg C21 or placebo) to be taken with a glass of water after minimum 2 hours fasting Afternoon/evening dose: Two 50 mg capsules (100 mg C21 or placebo) to be taken with a glass of water after minimum 2 hours fasting Subjects were required not to eat anything for 1 hour after taking the IMP.

Concomitant medication was given if in accordance with local standards of care (which did develop and/or change during the course of the study as more was discovered and/or understood about the pathology of COVID-1.9).

Subjects were not allowed to take the following medications at least 1 week before Visit 1 and during the trial period:

strong CYP3A4 inducers (e.g. rifampicin, phenytoin, St. John's Wort, phenobarbital, rifabutin, carbamazepine, anti HIV drugs, barbituates)

warfarin experimental drugs

As the skilled person will appreciate, in view of the nature of a new disease like COVID-19, where understanding of its pathology changes rapidly and continuously, and with treatment often being administered on an emergency and/or intensive care basis, the above protocol may not have been strictly adhered to in every single patient. Following an analysis of the results reported below, it is been confirmed that all such data collected from enlisted patients regarding safety and efficacy of C21, when considered individually or as part of a cohort, is valid.

Results

A total of 106 hospitalised patients with a diagnosis of coronavirus SARS-CoV-2 infection (confirmed by polymerase chain reaction test) and signs of an acute respiratory infection, but not requiring mechanical ventilation were recruited.

The patients were randomised to receive C21 (100 mg b.i.d., n=51) or placebo (n=56) for 7 days on top of standard of care. The treatment groups were well balanced in relation to both age and sex.

At the end of treatment, the number of patients that needed oxygen supply was 25 (45%) in the placebo group and 14 (27%) in the C21 group. This beneficial effect of C21 on need of oxygen supply was statistically significant at the predefined 10% level.

Moreover, there were 3 deaths in the placebo group and only 1 death in C21 group, and the number of patients needing mechanical ventilation was 4 in the placebo group compared to only 1 in the C21 group.

Considering the relatively small number of study subjects, these differences represent clear trends in favor of C21 treatment.

The study also demonstrated that C21 was well tolerated in this group of severely sick patients. The total number of reported adverse events was 90 in the placebo group and 64 in the C21 group.

There were no significant differences between the placebo group and the C21 group with regard to levels of the circulating biomarkers of inflammation CRP, IL-6 and TNF.

The invention claimed is:

1. A method of treating damage, injury, or dysfunction of respiratory tract mucosal tissue caused by a severe acute respiratory syndrome (SARS) coronavirus in a subject in need of such treatment, which method comprises administering N-butyloxycarbonyl-3-(4-imidazol-1-ylmethylphenyl)-5-isobutylthiophene-2-sulfonamide, or a pharmaceutically-acceptable salt thereof, to the subject in need of such treatment.

2. The method as claimed in claim 1, wherein the tissue is lung tissue.

3. The method as claimed in claim 1, wherein the tissue is the respiratory epithelium.

4. The method as claimed in claim 1, wherein the SARS coronavirus is severe acute respiratory syndrome coronavirus (SARS-CoV) or severe acute respiratory syndrome coronavirus 2 (SARS-CoV-2).

5. The method as claimed in claim 1, wherein the treatment includes treatment and/or arresting the progress of a respiratory disease that is being, or has been, caused by the SARS coronavirus.

6. The method as claimed in claim 5, wherein the respiratory disease is a severe acute respiratory syndrome.

7. The method as claimed in claim 5, wherein the respiratory disease is coronavirus disease 2019.

8. The method as claimed in claim 5, wherein the treatment includes treatment of the symptoms of the respiratory disease that is being, or has been, caused by the SARS coronavirus.

9. The method as claimed in claim 8, wherein the symptoms of the respiratory disease include one or more of cough, dyspnea, respiratory distress and/or respiratory failure.

10. The method as claimed in claim 8, wherein the symptoms of the respiratory disease include pneumonia.

11. The method as claimed in claim 8, wherein the symptoms of the respiratory disease include fibrosis in one or more internal organs selected from the lungs, the heart and/or the kidneys.

12. The method as claimed in claim 1, wherein the salt is a sodium salt.

13. The method as claimed in claim 9, wherein the respiratory distress is manifest by the need for supplementary oxygen and/or mechanical ventilation.

14. The method as claimed in claim 1, wherein said administering is carried out orally.

* * * * *